US012629017B2

(12) United States Patent

He et al.

(10) Patent No.: US 12,629,017 B2

(45) Date of Patent: May 19, 2026

(54) ANISOPLANATIC ABERRATION CORRECTION METHOD AND APPARATUS FOR ADAPTIVE OPTICAL BIAXIAL SCANNING IMAGING

(71) Applicant: Suzhou Institute of Biomedical Engineering and Technology, Chinese Academy of Sciences, Suzhou (CN)

(72) Inventors: Yi He, Suzhou (CN); Yiwei Chen, Suzhou (CN); Lina Xing, Suzhou (CN); Wen Kong, Suzhou (CN); Guohua Shi, Suzhou (CN)

(73) Assignee: Suzhou Institute of Biomedical Engineering and Technology, Chinese Academy of Sciences, Suzhou (CN)

( * ) Notice: Subject to any disclaimer, the term of this patent is extended or adjusted under 35 U.S.C. 154(b) by 692 days.

(21) Appl. No.: 18/083,453

(22) Filed: Dec. 16, 2022

(65) Prior Publication Data

US 2023/0190094 A1 Jun. 22, 2023

Related U.S. Application Data

(63) Continuation of application No. PCT/CN2021/100040, filed on Jun. 15, 2021.

(30) Foreign Application Priority Data

Jun. 16, 2020 (CN) .......................... 202010549873.3

(51) Int. Cl.
*A61B 3/10* (2006.01)
*A61B 3/14* (2006.01)

(52) U.S. Cl.
CPC .............. *A61B 3/1015* (2013.01); *A61B 3/14* (2013.01)

(58) Field of Classification Search
CPC ........... A61B 3/1015; A61B 3/14; A61B 3/12; A61B 3/1225

(Continued)

(56) References Cited

U.S. PATENT DOCUMENTS

| | | | | |
|---|---|---|---|---|
| 6,107,617 | A | * 8/2000 | Love | .......................... G01J 9/00 |
| | | | | 356/121 |
| 2019/0125178 | A1 | * 5/2019 | Murata | ................ A61B 3/1225 |

FOREIGN PATENT DOCUMENTS

| | | |
|---|---|---|
| CN | 102981269 A | 3/2013 |
| CN | 103393400 A | 11/2013 |

(Continued)

OTHER PUBLICATIONS

International Search Report of Corresponding International Application No. PCT/CN2021/100040 mailed Aug. 26, 2021, 7 pages.

(Continued)

*Primary Examiner* — William R Alexander
*Assistant Examiner* — Alaina Marie Swanson
(74) *Attorney, Agent, or Firm* — DINSMORE & SHOHL LLP

(57) ABSTRACT

An anisoplanatic aberration correction method and apparatus for adaptive optical biaxial scanning imaging are provided. Insofar as no adaptive optical wavefront sensor and wavefront corrector are added, an anisoplanatic aberration of biaxial scanning is divided into a plurality of isoplanatic sub-fields of view by means of a time-sharing method and according to a beam scanning trajectory; aberration measurement and closed-loop correction are respectively completed in each isoplanatic region sub-field of view, and a residual aberration of a formed image of each isoplanatic region sub-field of view is also supplementally corrected on the basis of an image processing technology, thereby realizing complete correction of an anisoplanatic aberration of a (Continued)

wide field of view. The aberration correction of a wide field of view can be completed only by a single wavefront sensor and a single wavefront corrector, so that the limitation of an isoplanatic region to an adaptive optical imaging field of view can be broken through, the aberration correction and high-resolution imaging of a wide field of view of a retina are realized, almost none of the system complexities is increased, and the method and the apparatus have extremely high practicability. The correction of an image subjected to deconvolution is low in cost, and the correction effect is good.

4 Claims, 3 Drawing Sheets

(58) Field of Classification Search
USPC ......................................................... 351/205
See application file for complete search history.

(56) References Cited

FOREIGN PATENT DOCUMENTS

| | | | | |
|---|---|---|---|---|
| CN | 105300941 A | * | 2/2016 | |
| CN | 105590300 A | * | 5/2016 | ............... G06T 5/70 |
| CN | 110794577 A | | 2/2020 | |
| JP | 6578429 B2 | * | 9/2019 | |

OTHER PUBLICATIONS

Written Opinion of the International Searching Authority of Corresponding International Application No. PCT/CN2021/100040 mailed Aug. 26, 2021, 10 pages.
First Office Action of Corresponding Chinese Application No. 202010549873.3 dated Jun. 20, 2022, 9 pages.

* cited by examiner

X

Y

| Sub-region 11 **H\*V°** | Sub-region 12 | • • • • • • | Sub-region 1N |
|---|---|---|---|
| | | | Sub-region 2N |
| | | | ⋮ |
| | | | Sub-region MN |

Fig.1

ANISOPLANATIC ABERRATION CORRECTION METHOD AND APPARATUS FOR ADAPTIVE OPTICAL BIAXIAL SCANNING IMAGING

TECHNICAL FIELD

The present application relates to the field of adaptive optical high-resolution imaging, in particular to an aniso-planatic aberration correction method and apparatus for adaptive optical biaxial scanning imaging.

BACKGROUND

In order to observe the fundus retina more clearly, adaptive optics has been introduced into the field of optical retinal imaging. The adaptive optics is used to measure and correct aberrations of an optical system of the eyes, so that high-resolution imaging of the fundus retina can be achieved, and micron-sized capillaries, visual cells and other tissues can be clearly distinguished.

However, the aberration measurement and correction of the adaptive optics can only be effective within an angle range near the center of the field of view. The angle range is defined as an "isoplanatic region" with a limited adaptive optical correction range. Aberrations in the isoplanatic region can be completely corrected by the adaptive optics, and anisoplanatic aberrations beyond the isoplanatic region can only be partially corrected by the adaptive optics. When the adaptive optics is applied to fundus retinal imaging, the isoplanatic region of the eyes is generally considered to have a field angle not exceeding 2°. At present, almost all adaptive optical retinal high-resolution imaging systems have an imaging field of view less than 2°, which is only equivalent to a very small region on the retina. In fact, a variety of fine tissues closely related to the visual function are distributed in the retina within about 100°. To complete high-resolution imaging of a larger range or the entire retina, multi-imaging is widely used at present to obtain a large-field image through image stitching, which is dependent on the visual fixation ability of a subject, resulting in low stitching precision, low success rate, and low efficiency.

In order to solve the problem of a small imaging field of view limited by the isoplanatic region of the eyes, Multi-Conjugate Adaptive Optics (MCAO) is applied to the field of astronomical observation. It was successfully used in the retinal floodlight imaging system for the first time in 2009. Multiple wavefront sensors and multiple wavefront correctors were used to realize regional measurement and simultaneous regional correction of aberrations of a 7° field of view. However, MCAO has a huge technical system structure and high technology cost; aberrations in adjacent isoplanatic regions overlap; and multiple sets of aberration correction closed-loop control has high complexity, and the imaging speed is low. More importantly, the MCAO is only applicable to a non-scanning floodlighting imaging system, and has not been reported to be applied to scanning imaging systems.

SUMMARY

Based on the above background, for a biaxial scanning imaging system (including a confocal scanning imaging system, an optical coherence tomography system and other biaxial scanning imaging systems), the present application provides an anisoplanatic aberration correction method and apparatus for adaptive optical biaxial scanning imaging.

Without adding an adaptive optical wavefront sensor and a wavefront corrector, an anisoplanatic aberration of biaxial scanning is divided into a plurality of isoplanatic sub-fields of view by means of a time-sharing method according to a beam scanning trajectory; aberration measurement and closed-loop correction are respectively completed in each isoplanatic sub-field of view, and a residual aberration of a formed image of each isoplanatic sub-field of view is also supplementally corrected on the basis of an image processing technology, thereby completely correcting an anisoplanatic aberration of a wide field of view. According to the anisoplanatic aberration correction method and apparatus provided by the present application, the aberration correction of the wide field of view can be completed only by a single wavefront sensor and a single wavefront corrector, which scarcely increasing the complexity of any of the systems. Therefore, the method and the apparatus have extremely high practicability.

The present application adopts the technical solution adopted as follows: an anisoplanatic aberration correction method for adaptive optical biaxial scanning imaging is provided. In the adaptive optical biaxial scanning imaging, biaxial scanning includes an X direction and a Y direction. The method includes the following steps:

step S1: dividing an entire anisoplanatic imaging field of view of the biaxial scanning into a plurality of sub-regions according to a scanning trajectory, the sub-regions including sub-region 11, sub-region 12, . . . , sub-region 1N, sub-region 21, sub-region 22, . . . , sub-region MN, wherein a field of view of each sub-region does not exceed 2° both in the X direction of scanning and the Y direction of scanning, and all the sub-regions satisfy the principle of an isoplanatic region; M and N are positive integers;

step S2: measuring an aberration of each isoplanatic sub-region by a wavefront sensor in sequence, and performing feedback in sequence to control a wavefront corrector to complete closed-loop correction of the aberration of each isoplanatic sub-region in sequence;

step S3: converting a wavefront aberration of each sub-region measured by the wavefront sensor to obtain a point spread function (PSF) of each sub-region, taking the PSF of each sub-region as a PSF initial value and constraint condition of a formed image of each sub-region, and respectively completing deconvolution processing of the formed image of each sub-region by means of Wiener filtering, so as to supplementally correct a residual aberration of the formed image of each sub-region; and step S4: after the deconvolution correction of the formed images of all the sub-regions is completed, stitching the images to obtain a formed image of a wide field of view with M×N sub-regions, the anisoplanatic aberration of which is completely corrected.

Preferably, in step S1, each sub-region may be uniformly and equally divided, or may be non-uniformly divided.

Preferably, step S3 specifically includes:

S3-1: performing calculation on a wavefront $W_{i,j}(\xi,\eta)$, $1{\le}i{\le}M$, $1{\le}j{\le}N$ of each sub-region measured by the wavefront sensor to obtain a PSF $h_{i,j}(x,y)$, $1{\le}i{\le}M$, $1{\le}j{\le}N$ of each sub-region, wherein $$h_{i,j}(x, y) = \left\| \int\int P_{i,j}(\xi, \eta)\exp\left(jkW_{i,j}(\xi, \eta)\right)\exp\left(-j\frac{k}{f}[(x\xi + y\eta)]\right)d\xi d\eta \right\|_2^2$$

$P_{i,j}(\xi,\eta)$ is a pupil function of a sub-lens of the wavefront sensor; f is a focal length of the sub-lens; k is a wave number constant; and S3-2: taking the PSF of each sub-region as a PSF initial value and constraint condition of a formed image of each sub-region, and respectively completing deconvolution processing of the formed image of each sub-region by means of the following iterative formula for incremental Wiener filtering, so as to supplementally correct a residual aberration of the formed image of each sub-region, $$\bar{X}_{i,j}^{new}(u,v) = \bar{X}_{i,j}^{old}(u,v) + \frac{\bar{H}_{i,j}^{*}(u,v)S(u,v)}{|\bar{H}_{i,j}(u,v)|^2 + \gamma_x};$$

$$\bar{H}_{i,j}^{new}(u,v) = \bar{H}_{i,j}^{old}(u,v) + \frac{\bar{X}_{i,j}^{*}(u,v)S(u,v)}{|\bar{X}_{i,j}(u,v)|^2 + \gamma_h};$$

$$S(u,v) = Y(u,,v) - \bar{X}_{i,j}(u,v)\bar{H}_{i,j}(u,v);$$

wherein * represents a complex conjugate operator; i and j represent the serial number of each sub-region; $Y_{i,j}$ (u,v) represents Fourier transformation of the formed image of the sub-region; $\bar{x}_{i,j}^{new}$(u,v) and $\bar{H}_{i,j}^{old}$(u,v) respectively represents Fourier transformations, iterated in the current deconvolution and the previous deconvolution, of the formed image of the sub-region; $\bar{H}_{i,j}^{new}$(u,v) and $\bar{H}_{i,j}^{old}$(u,v) respectively represent Fourier transformations, iterated in the current deconvolution and the previous deconvolution, of a PSF estimate of the sub-region; S(u,v) is a precision term; as values of $\bar{x}_{i,j}^{new}$(u,v) and $H_{i,j}^{new}$(u,v) are updated, the value of S(u,v) is updated timely; $r_x$ and $r_h$ are parameters for controlling an iteration step size; if the values of $\gamma_x$ and $\gamma_h$ are larger, the iteration step size is smaller, converging of the algorithm would be slower, and a solution thereof would be more accurate; and if the values of $\gamma_x$ and $\gamma_h$ decrease, the iteration step size increases, and the algorithm would converge faster into an unsmoothed solution.

Preferably, in step S3-2, the values of $\gamma_x$ and $\gamma_h$ are selected as: $\gamma_h=0.2|\hat{H}(0,0)|^2$, $\gamma_x=0.2|\hat{X}(0,0)|^2$.

Preferably, step S3 is carried out online or offline.

The present application further provides an anisoplanatic aberration correction apparatus for adaptive optical biaxial scanning imaging, wherein the apparatus is configured to adopt the above method to achieve anisoplanatic aberration correction for adaptive optical biaxial scanning imaging.

Preferably, the apparatus includes a light source and beam transformation system, a biaxial scanning system, an adaptive optical system, a beam collection system and a data processing system.

The light source and beam transformation system includes an imaging light source used for illumination imaging, a beacon light source used for aberration measurement, and an optical element used for transforming beams emitted by the imaging light source and the beacon light source.

The biaxial scanning system includes a scanning device capable of realizing beam scanning both in an X direction and in a Y direction; a scanning trajectory of the biaxial scanning system is configured to first scan the sub-regions along the X direction and then scans the sub-regions along the Y direction, or is configured to first scan the sub-regions along the Y direction and then scans the sub-regions along the X direction.

Preferably, the adaptive optical system includes a wavefront sensor, a wavefront corrector and a wavefront processor. The wavefront sensor is configured to measure a wavefront aberration and output the wavefront aberration to the wavefront processor. The wavefront processor is configured to solve the wavefront aberration into a wavefront control quantity, and perform feedback according to a scanning synchronization signal of the biaxial scanning system to control the wavefront corrector to generate phase compensation, so as to realize closed-loop correction of the wavefront aberration.

Preferably, the beam collection system includes an optical element used for completing focusing of imaging beams, and a detector for achieving photoelectric conversion.

Preferably, the data processing system is a digital processor or a computer. The data processing system is configured to complete, according to the scanning synchronization signal of the biaxial scanning system, image deconvolution on all the sub-regions on the scanning trajectory and image stitching on all the sub-regions having been subjected to the image deconvolution.

The present application has the beneficial effects:

According to the anisoplanatic aberration correction method and apparatus for adaptive optical biaxial scanning imaging provided by the present application, without adding the adaptive optical wavefront sensor and wavefront corrector, the anisoplanatic aberration of biaxial scanning is divided into a plurality of isoplanatic sub-fields of view by means of the time-sharing method according to the beam scanning trajectory. Aberration measurement and closed-loop correction are respectively completed in each isoplanatic sub-field of view, and the residual aberration of the formed image of each isoplanatic sub-field of view is also supplementally corrected on the basis of an image processing technology, thereby completely correcting the anisoplanatic aberration of the wide field of view.

In the present application, the aberration correction of the wide field of view can be completed only by a single wavefront sensor and a single wavefront corrector, so that the limitation of an isoplanatic region to an adaptive optical imaging field of view can be broken through, the aberration correction and high-resolution imaging of a wide field of view of the retina are realized, the complexity is scarcely increased for any of the systems, and the method and the apparatus have extremely high practicability.

The deconvolution image correction provided in the present application has low cost. The adaptive optical aberration correction can be maximally compensated by the regional deconvolution of wavefront aberration information. The correction effect is good. Both online processing and post-processing can be achieved, which are flexible and convenient.

BRIEF DESCRIPTION OF THE DRAWINGS

FIG. 1 is a schematic diagram of an anisoplanatic aberration correction method for adaptive optical biaxial scanning imaging in Embodiment 1 of the present application;

DETAILED DESCRIPTION

Figure 2:
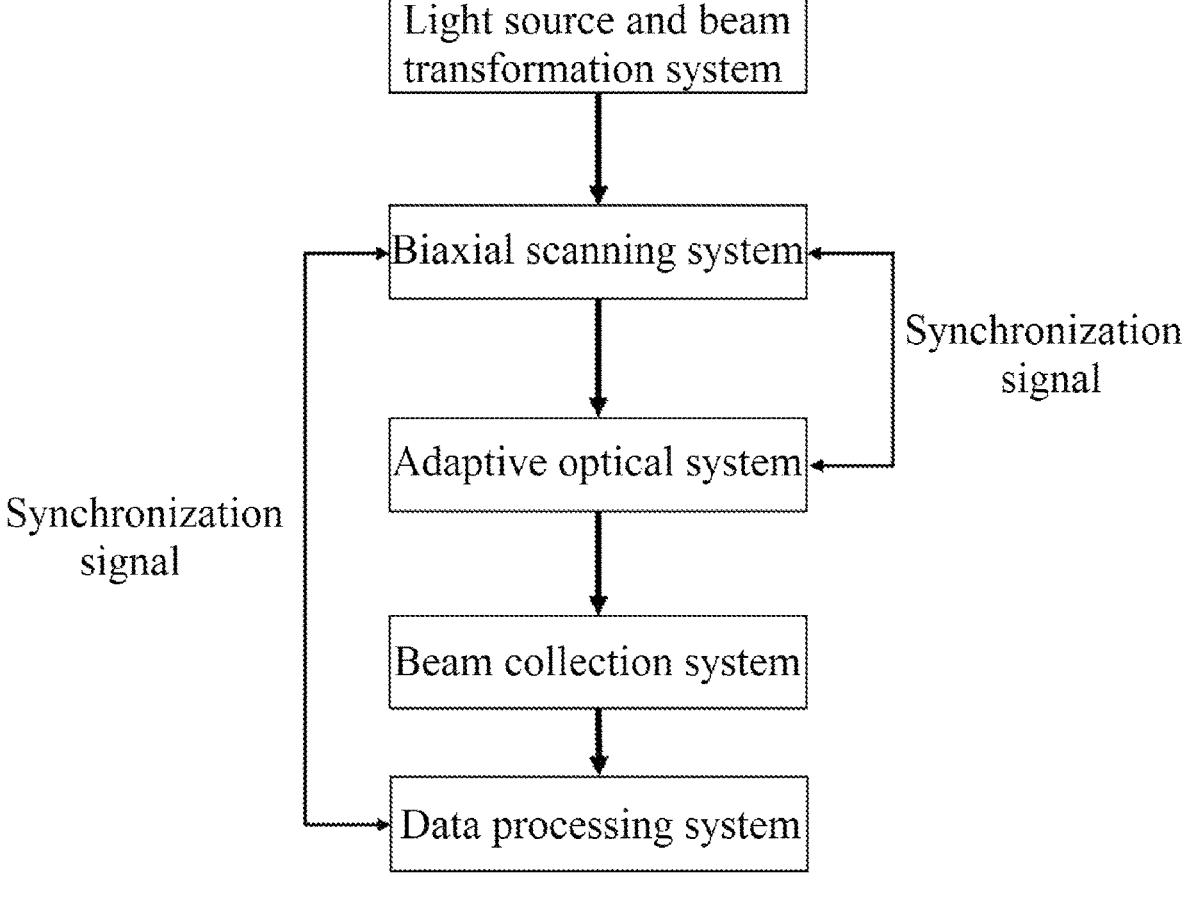
FIG. 2 is a schematic diagram of an anisoplanatic aberration correction apparatus for adaptive optical biaxial scanning imaging in Embodiment 2 of the present application.

The present application is further described in detail below in combination with the embodiments, so that those skilled in the art can implement the present application by referring to the text of this specification.

It should be understood that the terms such as "have", "comprise" and "include" used herein do not exclude the existence or addition of one or more other elements or combinations thereof.

Embodiment 1

In adaptive optical biaxial scanning imaging, biaxial scanning includes an X direction and a Y direction. Referring to FIG. 1, an anisoplanatic aberration correction method for adaptive optical biaxial scanning imaging provided by this embodiment includes the following steps.

Step S1: an entire anisoplanatic imaging field of view of the biaxial scanning is divided into a plurality of sub-regions according to a scanning trajectory, wherein the sub-regions including sub-region 11, sub-region 12, . . . , sub-region 1N, sub-region 21, sub-region 22, . . . , sub-region MN. A field of view of each sub-region does not exceed 2° both in the X direction of scanning and the Y direction of scanning, and all the sub-regions satisfy the principle of an isoplanatic region. As shown in FIG. 1, H and V respectively represent angle values of the field of view in the X direction of scanning and the Y direction of scanning, and are not greater than 2, and M and N are positive integers. Each sub-region can be uniformly and equally divided or non-uniformly divided.

Step S2: an aberration of each isoplanatic sub-region is measured by a wavefront sensor in sequence, and feedback is performed in sequence to control a wavefront corrector to complete closed-loop correction of the aberration of each isoplanatic sub-region in sequence.

Step S3: a wavefront aberration of each sub-region measured by the wavefront sensor is converted to obtain a PSF of each sub-region, the PSF of each sub-region is taken as a PSF initial value and constraint condition of a formed image of each sub-region, and the deconvolution processing of the formed image of each sub-region is respectively completed by means of Wiener filtering, so as to supplementally correct a residual aberration of the formed image of each sub-region.

Step 3 is specifically as follows:

S3-1: a wavefront $W_{i,j}(\xi,\eta)$, $1 \le i \le M$, $1 \le j \le N$ of each sub-region measured by the wavefront sensor is calculated to obtain a PSF $h_{i,j}(x,y)$, $1 \le i \le M$, $1 \le j \le N$ of each sub-region, wherein $$h_{i,j}(x, y) = \left\| \int \int P_{i,j}(\xi, \eta) \exp(jkW_{i,j}(\xi, \eta)) \exp\left(-j\frac{k}{f}[(x\xi + y\eta)]\right) d\xi d\eta \right\|_2^2$$

in the formula, $P_{i,j}(\xi,\eta)$ is a pupil function of a sub-lens of the wavefront sensor; f is a focal length of the sub-lens; k is a wave number constant.

S3-2: the PSF of each sub-region is taken as a PSF initial value and constraint condition of a formed image of each sub-region, and the deconvolution processing of the formed image of each sub-region is respectively completed by means of the following iterative formula for incremental Wiener filtering, so as to supplementally correct a residual aberration of the formed image of each sub-region, $$\hat{X}_{i,j}^{new}(u, v) = \hat{X}_{i,j}^{old}(u, v) + \frac{\hat{H}_{i,j}^*(u, v)S(u, v)}{|\hat{H}_{i,j}(u, v)|^2 + \gamma_x};$$

$$\hat{H}_{i,j}^{new}(u, v) = \hat{H}_{i,j}^{old}(u, v) + \frac{\hat{X}_{i,j}^*(u, v)S(u, v)}{|\hat{X}_{i,j}(u, v)|^2 + \gamma_h};$$

$$S(u, v) = Y(u, , v) - \hat{X}_{i,j}(u, v)\hat{H}_{i,j}(u, v);$$

wherein * represents a complex conjugate operator; i and j represent the serial number of each sub-region; $Y_{i,j}$ (u,v) represents Fourier transformation of the formed image of the sub-region;

$$\hat{X}_{i,j}^{new}(u, v) \text{ and } \hat{X}_{i,j}^{old}(u, v)$$

respectively represents Fourier transformations, iterated in the current deconvolution and the previous deconvolution, of the formed image of the sub-region;

$$\hat{H}_{i,j}^{new}(u, v) \text{ and } \hat{H}_{i,j}^{old}(u, v)$$

respectively represent Fourier transformations, iterated in the current deconvolution and the previous deconvolution, of a PSF estimate of the sub-region; S(u,v) is a precision term; as values of $$\hat{X}_{i,j}^{new}(u, v) \text{ and } \hat{H}_{i,j}^{new}(u, v)$$

are updated, the value of S(u,v) is updated timely; $\gamma_x$ and $\gamma_h$ are parameters for controlling an iteration step size; if the values of $\gamma_x$ and $\gamma_h$ are larger, the iteration step size is smaller, converging of the algorithm would be slower, and a solution thereof would be more accurate; and if the values of $\gamma_x$ and $\gamma_h$ decrease, the iteration step size increases, and the algorithm would converge faster into an unsmoothed solution. Values of $\gamma_x$ and $\gamma_h$ may be selected as: $\gamma_h = 0.2|\hat{H}(0,0)|^2$, $\gamma_x = 0.2|\hat{X}(0,0)|^2$.

Step S3 can be carried out online or offline.

Step S4: after the deconvolution correction of the formed images of all the sub-regions is completed, the images are stitched to obtain a formed image of a wide field of view with M×N sub-regions, the anisoplanatic aberration of which is completely corrected.

Embodiment 2

An anisoplanatic aberration correction apparatus for adaptive optical biaxial scanning imaging is provided. The apparatus is configured to adopt the method of Embodiment 1 to achieve anisoplanatic aberration correction for adaptive optical biaxial scanning imaging. Specifically, referring to FIG. 2, the apparatus includes a light source and beam transformation system, a biaxial scanning system, an adaptive optical system, a beam collection system and a data processing system.

The light source and beam transformation system includes an imaging light source used for illumination imaging, a beacon light source used for aberration measurement, and an optical element used for transforming beams emitted by the imaging light source and the beacon light source. The light source and beam transformation system can also include light sources with other imaging functions.

The biaxial scanning system includes a scanning device capable of realizing beam scanning both in an X direction and in a Y direction; a scanning trajectory of the biaxial scanning system is configured to first scan the sub-regions along the X direction and then scans the sub-regions along the Y direction, or is configured to first scan the sub-regions along the Y direction and then scans the sub-regions along the X direction.

The adaptive optical system includes a wavefront sensor, a wavefront corrector and a wavefront processor. The wavefront sensor is configured to measure a wavefront aberration and output the wavefront aberration to the wavefront processor. The wavefront processor is configured to solve the wavefront aberration into a wavefront control quantity, and perform feedback according to a scanning synchronization signal of the biaxial scanning system to control the wavefront corrector to generate phase compensation, so as to realize closed-loop correction of the wavefront aberration.

The beam collection system includes an optical element used for completing focusing of imaging beams, and a detector for achieving photoelectric conversion. The beam collection system can have a variety of combinations, including a confocal imaging mode, a time-domain optical coherence tomography mode, a spectral-domain optical coherence tomography mode, or a Fourier-domain optical coherence tomography mode, or the like.

The data processing system is a digital processor or a computer, and is configured to complete, according to the scanning synchronization signal of the biaxial scanning system, image deconvolution on all the sub-regions on the scanning trajectory and image stitching on all the sub-regions having been subjected to the image deconvolution.

Figure 3:
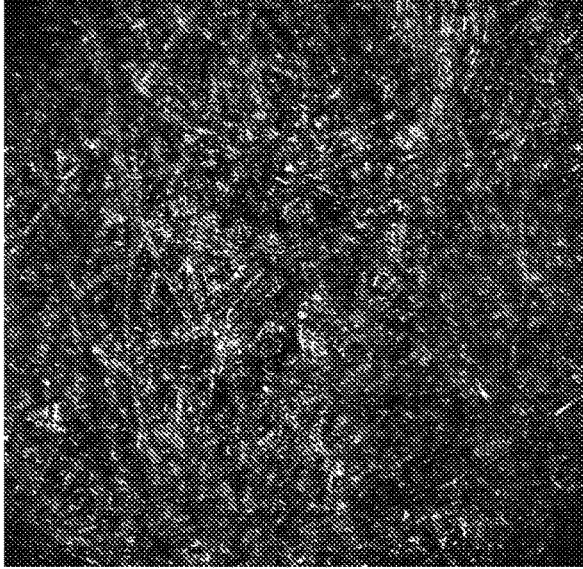
FIG. 3 is a conventional single adaptive optical closed-loop correction aberration result in Embodiment 3 of the present application.

Embodiment 3 Comparison Between the Conventional Correction Method and the Method of the Present Application Referring to FIG. 3 which illustrates a conventional single adaptive optical closed-loop correction aberration result, an imaging field of view is 4*4 degrees, and a central isoplanatic region of 2*2 degrees has a good aberration correction effect. Other edge fields of view are anisoplanatic regions, the aberration correction is incomplete, and the image is fuzzy.

Figure 4:
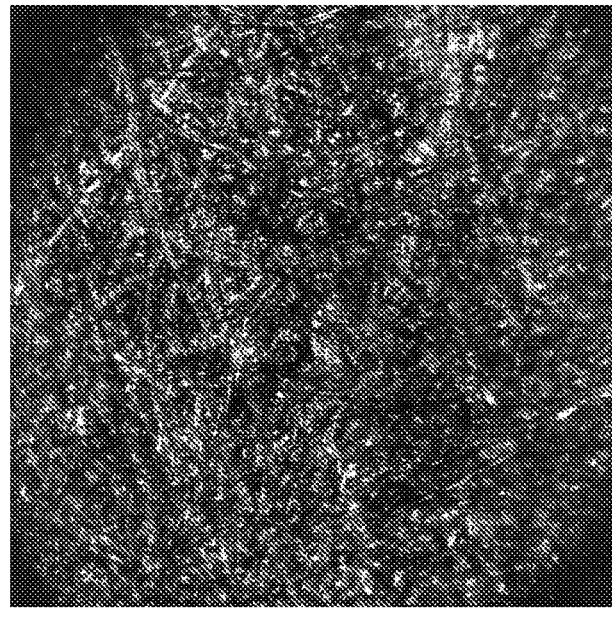
FIG. 4 is a result of regional adaptive optical correction on an anisoplanatic aberration provided by the present application in Embodiment 3 of the present application.
Figure 5:
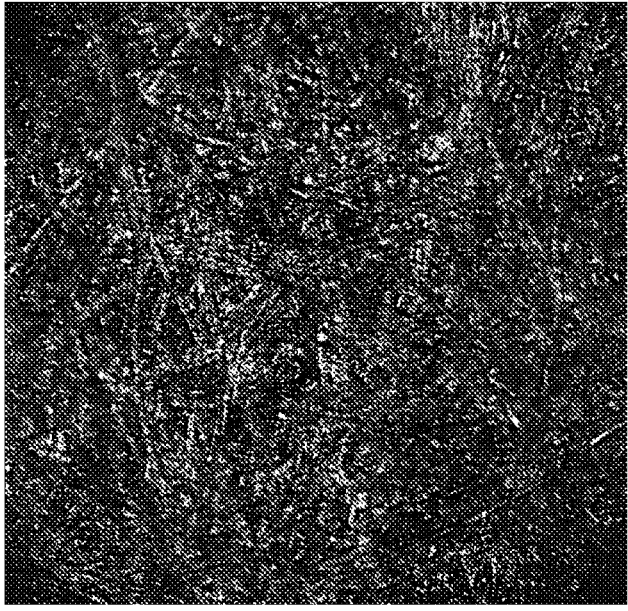
FIG. 5 is a regional image deconvolution processing result in Embodiment 3 of the present application.

Referring to FIG. 4 which illustrates a result of regional adaptive optical correction on an anisoplanatic aberration provided by the present application, the entire imaging field of view of 4*4 degrees is divided into four imaging sub-regions of 2*2 degrees to complete aberration correction in sequence. Referring to FIG. 5 which illustrates an effect of regional deconvolution processing of images provided by the present application, after the regional adaptive optical aberration correction in FIG. 4 is completed, deconvolution processing is continued, so as to complete the deconvolution processing of the images in four sub-regions by Wiener filtering respectively, which can correct the residual aberration of the images.

Although the implementation solutions of the present application have been disclosed as above, it is not limited to the applications listed in the specification and the implementations. The present application can be fully applied to various fields suitable for the present application. Those skilled in the art can easily implement additional modifications. Therefore, the present application is not limited to specific details without departing from the general concept defined by the claims and the equivalent scope.

What is claimed is:

1. An anisoplanatic aberration correction system for adaptive optical biaxial scanning imaging comprising:

an imaging light source for illumination imaging, a beacon light source for aberration measurement, and an optical element for transforming the light beams emitted by the imaging light source and the beacon light source;

a scanning device capable of realizing light beam scanning in the X and Y directions;

a wavefront sensor, a wavefront corrector, and a wavefront processor, wherein the wavefront sensor realizes the measurement of wavefront aberration and outputs it to the wavefront processor; the wavefront processor solves the wavefront aberration into a wavefront control quantity, and then performs feedback control on the wavefront corrector according to the scanning synchronization signal of the scanning device to generate phase compensation, thereby realizing closed-loop correction of the wavefront aberration;

an optical element for completing the focusing of imaging light beams and a detector for realizing photoelectric conversion;

a digital processor, which is used for completing image deconvolution processing for all sub-regions on the scanning trajectory and image stitching for all sub-regions after image deconvolution processing according to the scanning synchronization signal of the scanning device;

wherein the system executes the following steps:

step S1: by the scanning device, dividing an entire anisoplanatic imaging field of view of the biaxial scanning into a plurality of sub-regions according to a scanning trajectory, the sub-regions including sub-region 11, sub-region 12, . . . , sub-region 1N, sub-region 21, sub-region 22, . . . , sub-region MN, wherein a field of view of each sub-region does not exceed 2° both in the X direction of scanning and in the Y direction of scanning, and all the sub-regions satisfy the principle of an isoplanatic region; M and N are positive integers;

step S2: measuring an aberration of each isoplanatic sub-region by a wavefront sensor in sequence, and performing feedback in sequence to control a wavefront corrector to complete closed-loop correction of the aberration of each isoplanatic sub-region in sequence;

step S3: converting a wavefront aberration of each sub-region measured by the wavefront sensor to obtain a point spread function (PSF) of each sub-region, taking the PSF of each sub-region as a PSF initial value and constraint condition of a formed image of each sub-region, and respectively completing deconvolution processing of the formed image of each sub-region by means of Wiener filtering, so as to supplementally correct a residual aberration of the formed image of each sub-region; and step S4: after the deconvolution correction of the formed images of all the sub-regions is completed, stitching the images to obtain a formed image of a wide field of view with M×N sub-regions, the anisoplanatic aberration of which is completely corrected;

wherein step S3 specifically comprises:

S3-1: performing calculation on a wavefront $W_{i,j}(\xi,\eta)$, $1\leq i\leq M, 1\leq j\leq N$ of each sub-region measured by the wavefront sensor to obtain a PSF $h_{i,j}(x,y)$, $1\leq i\leq M$, $1\leq j\leq N$ of each sub-region, wherein $$h_{i,j}(x,y) = \left\| \int\int P_{i,j}(\xi,\eta)\exp(jkW_{i,j}(\xi,\eta))\exp\left(-j\frac{k}{f}[(x\xi+y\eta)]\right)d\xi d\eta \right\|_2^2$$

$P_{i,j}(\xi,\eta)$ is a pupil function of a sub-lens of the wavefront sensor; f is a focal length of the sub-lens; k is a wave number constant; and S3-2: taking the PSF of each sub-region as a PSF initial value and constraint condition of a formed image of each sub-region, and respectively completing deconvolution processing of the formed image of each sub-region by means of the following iterative formula for incremental Wiener filtering, so as to supplementally correct a residual aberration of the formed image of each sub-region, $$\bar{X}_{i,j}^{new}(u,v) = \bar{X}_{i,j}^{old}(u,v) + \frac{\bar{H}_{i,j}^*(u,v)S(u,v)}{\left|\bar{H}_{i,j}(u,v)\right|^2 + \gamma_x};$$

$$\bar{H}_{i,j}^{new}(u,v) = \bar{H}_{i,j}^{old}(u,v) + \frac{\bar{X}_{i,j}^*(u,v)S(u,v)}{\left|\bar{X}_{i,j}(u,v)\right|^2 + \gamma_h};$$

$$S(u,v) = Y(u,,v) - \bar{X}_{i,j}(u,v)\bar{H}_{i,j}(u,v);$$

wherein * represents a complex conjugate operator; i and j represent the serial number of each sub-region; $Y_{i,j}$

10

(u,v) represents Fourier transformation of the formed image of the sub-region; $\bar{X}_{i,j}^{new}$(u,v) and $\bar{H}_{i,j}^{old}$(u,v) respectively represents Fourier transformations, iterated in the current deconvolution and the previous deconvolution, of the formed image of the sub-region;

$\bar{H}_{i,j}^{new}$(u,v) and $\bar{H}_{i,j}^{old}$(u,v) respectively represent Fourier transformations, iterated in the current deconvolution and the previous deconvolution, of a PSF estimate of the sub-region; S(u,v) is a precision term; as values of $\bar{X}_{i,j}^{new}$(u,v) and $\bar{H}_{i,j}^{old}$(u,v) are updated, the value of S(u,v) is updated timely; $\gamma_x$ and $\gamma_h$ are parameters for controlling an iteration step size; if the values of $\gamma_x$ and $\gamma_h$ are larger, the iteration step size is smaller, converging of the algorithm would be slower, and a solution thereof would be more accurate; and if the values of $\gamma_x$ and $\gamma_h$ decrease, the iteration step size increases, and the algorithm would converge faster into an unsmoothed solution.

2. The anisoplanatic aberration correction system for adaptive optical biaxial scanning imaging according to claim 1, wherein, in step S1, each sub-region may be uniformly and equally divided, or may be non-uniformly divided.

3. The anisoplanatic aberration correction system for adaptive optical biaxial scanning imaging according to claim 1, wherein in step S3-2, the values of $\gamma_x$ and $\gamma_h$ are selected as:

$$\gamma_h = 0.2|\hat{H}(0,0)|^2, \quad \gamma_x = 0.2|\hat{X}(0,0)|^2.$$

4. The anisoplanatic aberration correction system for adaptive optical biaxial scanning imaging according to claim 1, wherein step S3 is carried out online or offline.

* * * * *